United States Patent [19]

Benfatto et al.

[11] Patent Number: 5,376,363
[45] Date of Patent: Dec. 27, 1994

[54] CLEAR GELLED ANTIPERSPIRANT STICK COMPOSITION

[75] Inventors: Anthony J. Benfatto, North Brunswick; Daniel M. Grabois, Edison; Chung T. Shin, Livingston; Robert Stillman, Edison, all of N.J.

[73] Assignee: Bristol-Myers Squibb Company, New York, N.Y.

[21] Appl. No.: 67,889

[22] Filed: May 27, 1993

Related U.S. Application Data

[63] Continuation-in-part of Ser. No. 844,041, Mar. 2, 1992, abandoned, which is a continuation-in-part of Ser. No. 700,378, May 3, 1991, abandoned, and a continuation-in-part of Ser. No. 700,381, May 3, 1991, abandoned.

[51] Int. Cl.$^5$ .......................... A61K 7/32; A61K 7/34; A61K 7/38
[52] U.S. Cl. .................. 424/66; 424/DIG. 5; 424/65; 424/68
[58] Field of Search ............... 424/66, DIG. 5, 68

[56] References Cited

U.S. PATENT DOCUMENTS

| | | | |
|---|---|---|---|
| 4,719,102 | 1/1988 | Randhawa et al. | 424/66 |
| 4,722,835 | 2/1988 | Schamper et al. | 424/66 |
| 4,725,430 | 2/1988 | Schamper et al. | 424/66 |

*Primary Examiner*—Dale R. Ore
*Attorney, Agent, or Firm*—M. S. Simon

[57] ABSTRACT

The invention provides stable, substantially anhydrous, transparent, gelled cosmetic compositions useful for the preparation of deodorant and antiperspirant sticks which are substantially free of lower, aliphatic, monohydroxy alcohols. The compositions contain dibenzylidene monosorbitol acetal as a gelling agent and are stabilized by the presence of an inorganic base.

8 Claims, No Drawings

CLEAR GELLED ANTIPERSPIRANT STICK COMPOSITION

RELATED APPLICATIONS

This application is a continuation-in-part of copending application Ser. No. 07/844,041 filed Mar. 2, 1992, now abandoned which is, in turn, a continuation-in-part application based partly on each of applications serial numbers 07/700,378 and 07/700,381, both filed on May 3, 1991. Both of which are now abandoned.

BACKGROUND OF THE INVENTION

1. Field of the Invention

The cosmetic compositions of this invention are particularly useful for preparing antiperspirant sticks and deodorant sticks.

2. Description of the Related Art

Gelled antiperspirant compositions for use in preparing transparent antiperspirant sticks are known. Typically, they will contain an antiperspirant, a solvent and a gelling agent, although other ingredients such as perfumes, coloring agents, antibacterial agents and emollients may be present.

Gelled deodorant compositions using sodium stearate and propylene glycol for preparing non-transparent deodorant sticks are known. As deodorant sticks, they generally function in one of two ways. Either they contain a strong fragrance such as a perfume which masks body odor caused by bacteria which multiply using perspiration as a nutrient medium, or they provide a hostile environment for bacterial growth because they contain an anti-bacterial agent and they are strongly alkaline.

It is impossible to make acidic gelled sticks using sodium stearate and propylene glycol base, because these compounds are not compatible with acidic antiperspirant salts. Sodium stearate no longer functions as a gelling agent in propylene glycol at acidic pH. Therefore, commercial deodorant sticks which have an acidic pH are not available except as opaque, antiperspirant sticks. Clear, transparent, deodorant sticks having an acidic pH are not available due to formulation difficulties.

DBMSA (dibenzylidene monosorbitol acetal) is particularly favored as a gelling agent in transparent gelled sticks. However, DBMSA is unstable in the presence of acids and hydrolyzes to form benzaldehyde. Benzaldehyde has an almond like odor which, while not necessarily unpleasant, is undesirable because it indicates the hydrolytic decomposition of DBMSA which is generally accompanied by decreased color and odor stability.

Antiperspirant compositions contain astringent aluminum or zirconium compounds or complexes or mixtures thereof. Usually the aluminum or zirconium compounds will take the form of astringent salts.

Such compounds are of a class well known in the art. They are described, for example, in Miller and Hoag, Personal Care Products, Handbook of Nonprescription Drugs, 5th Ed., Chapter 19, pages 397-417 (American Pharmaceutical Association, 1986). Aluminum compounds are described in U.S. Pat. Nos. 3,887,692; 3,904,741 and 4,359,456; and in British Patent Specifications 2,048,229 and 1,347,950. Zirconium compounds are described in U.S. Pat. Nos. 3,679,068 and 4,120,948. All of these citations are incorporated herein by reference. Attention is also directed to the Antiperspirant OTC Monograph which discloses antiperspirant salts commonly employed in antiperspirant compositions.

Many of the commonly employed aluminum or zirconium salts are acidic and, as aforesaid, DBMSA is unstable in acidic compositions. Much effort has been expended to stabilize DBMSA in acidic compositions against hydrolytic decomposition to benzaldehyde and other products.

U.S. Pat. No. 4,719,102 describes the use of various stabilizing agents such as N-(2-hydroxyethyl) fatty ($C_8$-$C_{12}$) acid amide, magnesium sulfate, zinc acetate and hexamethylenetetramine. The last three of these compounds are also described as stabilizers in U.S. Pat. Nos. 4,518,582 and 4,720,381.

U.S. Pat. No. 4,725,430 describes the use of N-(2-hydroxyethyl) acetamide, alone, or combined with one or more of magnesium sulfate, zinc acetate, N-(2-hydroxyethyl) cocamide and hexamethylenetetramine as stabilizers in ethanolic compositions.

U.S. Pat. No. 4,722,835 describes the use of basic metallic salts such as calcium hydroxide and potassium carbonate as stabilizers for antiperspirant stick compositions. The compositions of the patent include 1 to 50% of what are described as small, polar organic and organic compatible compounds such as morpholine, pyridine and acetic acid as well as ethanol, propanol and butanol. The compositions may also contain less reactive alcohols which are secondary or long chain primary alcohols, such as isopropanol, isobutanol and 1,2-butylene glycol. The compositions are described as opaque.

Such stabilizing agents as have heretofore been utilized have not proved to be completely satisfactory principally due to discoloration and/or lack of clarity.

Other U.S. Patents describing the use of DBMSA as a gelling agent include 4,137,306; 4,154,816; 4,720,381; 4,781,917; 4,346,079; 4,822,602; 4,822,603; and 4,816,261. Foreign patent documents which relate to such compositions include Japanese Patent Publication 23170/88, which describes the use of urea as an anti-gelling agent, and European Patent Applications 0272919 and 0274267.

Many of these patents describe the use of water and lower monohydric alcohols, such as ethanol, as solvents. Such solvents are best avoided in gel stick compositions because sticks containing a high concentration of alcohol have a tendency to shrink due to evaporation of the alcohol. Additionally, it is difficult to prepare a clear antiperspirant stick due to the high temperatures required to solubilize DBMSA in alcohol. Water and ethyl alcohol are especially unsatisfactory solvents because they are very reactive, increase the rate of hydrolysis of DBMSA and heighten the almond odor. They also reduce stick hardness and increase tackiness.

As will be understood from the following description, the compositions of this invention are substantially anhydrous and substantially lower aliphatic monohydroxy alcohol free and yet, are highly transparent i.e. clear. Small amounts of water and/or alcohol can be added to the compositions of the present invention without adversely affecting stability. However, the compositions become more and more difficult to manufacture if alcohol is present. Additionally, too much water may cause a loss of clarity. Thus, although operative, the inclusion of alcohol and water in the compositions of the present invention is not preferred.

"Substantially free" relative to the water and lower monohydroxy alcohols as used herein means the composition contains less than about 5% and preferably 0% of such materials. The term does not include the presence of bound water.

As used in this description and claims the term "stable" means that samples of the product, in stick form, when stored for one month at 104° F. will not exhibit a noticeable or objectionable benzaldehyde odor or color instability indicative of hydrolysis of DBMSA and will retain stick transparency and stick shape.

The term "lower aliphatic monohydroxy alcohols" means alcohols containing up to six carbon atoms such as methanol or ethanol.

The compositions of the present invention are transparent to the transmission of light. By transparent is meant that sufficient light passes through the gel sticks of the present invention to enable an observer to see without difficulty an image, e.g., lettering, placed immediately behind and in contact with the gel stick.

The compositions of this invention take two principal forms. In one form, they are useful for preparing antiperspirant sticks. In the other, they are useful for preparing deodorant sticks. For the former utility, they are principally characterized in that they contain an antiperspirant amount of an acidic antiperspirant soluble in the composition. For the latter utility, they contain up to about 8% of such antiperspirant together with an odor masking perfume and/or an antibacterial agent.

SUMMARY OF THE INVENTION

Stable, substantially anhydrous (preferably anhydrous) and substantially lower aliphatic monohydroxy alcohol free (preferably completely free) transparent, gelled, cosmetic compositions have now been discovered which are gelled by DBMSA, may contain acidic antiperspirants, and utilize dihydroxy aliphatic alcohols containing 3 to 6 carbon atoms as solvents. In the compositions, the DBMSA is stabilized against hydrolysis and the formation of benzaldehyde by the presence of a stabilizing amount of a selected inorganic base. The pH of the compositions is from about 3.5 to about 4.9, preferably 4.0 to 4.8.

The compositions of the invention will be employed in the same manner as other similar compositions. They may, for example, be formed into sticks and applied to the axilla to inhibit perspiration and/or odor.

In this disclosure and the appended claims, unless otherwise stated, all concentrations are in weight percent based on the total weight of the composition.

DETAILED DESCRIPTION OF THE INVENTION

The antiperspirant employed in the compositions of the invention may be any of the astringent, acidic, metallic salts generally utilized in such compositions provided that they are soluble in the compositions under the conditions of use. Suitable products which may be mentioned by way of example are aluminum chlorohydroxide, aluminum chloride, aluminum sesquichlorohydroxide, zirconyl hydroxychloride, and the aluminum chlorohydrol-propylene glycol complex (ACH-Propylene Glycol Complex). The last named product is commercially available, for example, as Rehydrol II from Reheis Chemical Company. The preferred antiperspirants are aluminum zirconium polychlorohydrates (especially when complexed with glycine for example, aluminum zirconium trichlorohydrate glycine) and the corresponding tetrachlorohydrate complex.

For antiperspirant compositions, the amount of antiperspirant employed will be the same as normally employed in antiperspirant compositions. Such amount is described herein as an "antiperspirant quantity". Typically the amount will be on an active basis, from 8 to about 25%, preferably about 10 to about 16%.

For deodorant compositions the amount of antiperspirant may be less than 8%.

Certain of the antiperspirant salts employed in the invention are strongly acidic for example, aluminum chloride and zirconium hydroxy chloride. They may be employed provided the pH of the composition is increased to the desired range by the use of additional alkaline stabilizer or by the use of a buffer, suitably glycine.

Typical aluminum salts employed for the preparation of the compositions of the invention may be represented by the formula:

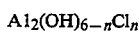

$$Al_2(OH)_{6-n}Cl_n$$

in which n is from 0.8 to 2. In the preferred compound of the series n is 1. Such aluminum salts are available from Reheis Chemical Company.

The preferred antiperspirants of the invention, as stated above, are aluminum zirconium polychlorohydrate complexes with glycine. They may be represented by the formula:

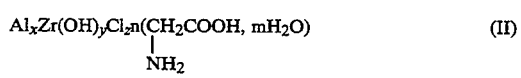

$$Al_xZr(OH)_yCl_z n(\underset{\underset{NH_2}{|}}{CH_2COOH}, mH_2O) \qquad (II)$$

wherein:
(a) x is a number from 2 to 10:
(b) z is a number from 3 to 8;
(c) y equals (3x+4)-z;
(d) the sum of y+z is a number from 10 to 34;
(e) m is a number from 0 to 12;
(f) n is a number from 0 to 3 y ordinarily will have a value of from about 5 to about 29.

As will be clear from the formula II, the glycine may be bound in the complex or it may be absent. The presence or absence of the glycine in the complex will determine the amount of unbound glycine or other buffer that may be incorporated in the composition to increase the pH to the desired level.

A number of aluminum zirconium polychlorohydrate complexes known in the prior art are useful for the present purposes. By way of example, the following may be mentioned along with their empirical formulas: aluminum zirconium tetrachlorohydrate ($Al_4Zr(OH)_{12}Cl_4$); aluminum zirconium tetrachlorohydrate glycine (Dow Corning AZG-369) ($Al_4Zr(OH)_{12}Cl_4$ $NH_2CH_2COOH$); aluminum zirconium trichlorohydrate ($Al_4Zr(OH)_{13}Cl_3$; aluminum zirconium trichlorohydrate glycine ($Al_4Zr(OH)_{13}Cl_3$ $NH_2CH_2COOH$); aluminum zirconium pentachlorohydrate ($Al_{10}Zr(OH)_{29}Cl_5$); aluminum zirconium pentachlorohydrate glycine ($Al_{10}Zr(OH)_{29}Cl_5$ $NH_2CH_2COOH$); aluminum zirconium octachlorohydrate ($Al_{16}Zr(OH)_{14}Cl_8$); and aluminum zirconium octachlorohydrate glycine ($Al_{16}Zr(OH)_{14}Cl_8$ $NH_2CH_2COOH$). The aluminum zirconium polychlorohydrate complex can be mixed individually with the ACH (alluminum chlorhydrate) and $AlCl_3$ $6H_2O$ in solution or powder form or in various combinations thereof.

The Food and Drug Administration's OTC Panel On Antiperspirants has adopted certain nomenclature and specifications for various aluminum zirconium polychlorohydrates that are useful in the present invention. These are set out in Table A below:

TABLE A

| Panel Adopted Nomenclature | Metal-Halide Ratio Range | Al/Zr Ratio Range |
|---|---|---|
| Aluminum zirconium trichlorohydrate | 2.1 down to but not including 1.5:1 | 2.0 up to but not including 6.0:1 |
| Aluminum zirconium tetrachlorohydrate | 1.5 down to and including 0.9:1 | 2.0 up to but not including 6.0:1 |
| Aluminum zirconium pentachlorohydrate | 2.1 down to but not including 1.5:1 | 6.0 up to and including 10.0:1 |
| Aluminum zirconium octachlorohydrate | 1.5 down to and including 0.9:1 | 6.0 up to and including 10.0:1 |

A number of the aluminum zirconium polychlorohydrate complexes that are useful in the present invention are available commercially. Reheis Chemical Company promotes a series of materials under the general trademark REZAL ™. The following Table describes a number of these products together with their specifications:

TABLE 1

1 REZAL 36G Aluminum zirconium tetrachlorohydrate Gly (soln.)
2 REZAL 36 Aluminum zirconium trichlorohydrate (pdr.)
3 REZAL 67 Aluminum zirconium pentachlorohydrate (soln.)
4 REZAL 67 Aluminum zirconium pentachlorohydrate (pdr.)

|  | 1 | 2 | 3 | 4 |
|---|---|---|---|---|
| Approx. Al/Zr ratio | 3.6:1 | 3.6:1 | 6.7:1 | 6.7:1 |
| Approx. metal/Cl ratio | 1.4:1 | 1.6:1 | 1.7:1 | 1.7:1 |
| Concentration of solids | 35% | 100% | 40% | 100% |
| Aluminum(Al) | 5.0%–5.7% | 16.3%–17.7% | 7.6%–8.4% | 19.0%–21.0% |
| Zirconium(Zr) | 4.4%–5.7% | 13.8%–15.2% | 3.7%–4.3% | 9.2%–10.8% |
| Glycine | 3.6%–4.7% | — | — | — |
| Chloride(Cl) | 5.9%–6.7% | 16.0%–19.0% | 6.5%–7.2% | 16.2%–18.0% |
| Iron(Fe) | NMT 50 ppm | NMT 100 ppm | NMT 50 ppm | NMT 100 ppm |
| Heavy metals (as Pb) | NMT 10 ppm | NMT 20 ppm | NMT 10 ppm | NMT 20 ppm |
| Particle size (thru 325 mesh) | — | 97% min. | — | 97% min. |

Similar products are marketed by Dow Corning and the Westwood Chemical Company.

DBMSA GELLING AGENT

DBMSA is available commercially as Gell All-D from the New Japan Chemical Co. Ltd., Osaka or as Millithix 925 from Milliken Chemical, Division of Milliken & Company. It is employed in an amount which will be sufficient to gel the hereinafter described compositions. Although there may be appreciable variation in the amount of DBMSA necessary to form a gel in a specific composition, it has been observed that from about 1.5 to 5%, preferably about 1.8 to 3.0%, is generally sufficient.

SOLVENT

Solvents and cosolvents for the compositions of the invention are employed to solubilize the gellant, oils, surfactants and other components of the compositions to produce miscible products which can be formed into transparent gels. They are selected from dihydroxy aliphatic alcohols containing from 3 to 5 carbon atoms. These include, for example, 1,3-propylene glycol; 1,2-propylene glycol; 1,3-butylene glycol; 1,4-butylene glycol; and 1,5-dihydroxy pentane. The presently preferred solvent is 1,2-propylene glycol. The amount of solvent employed will be the quantity necessary to dissolve the antiperspirant in the presence of the other components of the compositions, although auxiliary solvents or cosolvents, other than water or lower monohydroxy alkanols, may be employed, as will be discussed below. Typically, the compositions of the invention will contain from about 41% to about 75%, preferably about 51% to about 70%, of the dihydroxy alcohol solvent.

STABILIZER

The stabilizer is an essential component of the compositions of the invention. Surprisingly, if the instant compositions do not contain the required stabilizer, a gelled stick will not form. Inorganic alkaline reagents used in the practice of this invention include alkali and alkaline earth metal oxides, hydroxides, carbonates or bicarbonates and trivalent metallic hydroxides such as aluminum hydroxide or aluminum magnesium hydroxide. These include, for example, sodium and potassium hydroxides, carbonates and bicarbonates as well as calcium and magnesium oxides, hydroxides and carbonates, provided they are soluble in the compositions. The preferred stabilizers are sodium and potassium hydroxides and sodium bicarbonate because they are readily available at relatively low cost and, because they work well. Typically, the stabilizer will be employed in a weight percent range of from about 0.1 to 2.0, preferably 0.4 to 1.5. With sodium and potassium hydroxide, the range is 0.2 to 1.9, and the preferred range is 0.5 to 1.0. For sodium bicarbonate the range is 0.1 to 2.0, preferably 0.5 to 1.8. Mixtures of inorganic bases can be employed.

As will be seen from the examples, the stabilizer is mixed in to the composition before the DBMSA. This order of addition promotes the production of clear compositions.

The amount of stabilizer used in the compositions of the invention depends on the acidity of the antiperspirant salt and the basicity of the stabilizer. The more acidic salts require larger amounts of the alkaline stabilizer. When a more basic stabilizer is used lesser amounts of stabilizer are required for the same antiperspirant salt. The optimum ratio of antiperspirant salt to stabilizer is readily determinable for each formulation.

COSOLVENT

Cosolvents may be employed to assist in dissolving the components in the compositions of the invention.

By far the most preferred cosolvent is dipropylene glycol, although other dihydroxy aliphatic ethers, containing from 6 to 10 carbon atoms such as dibutylene glycol, may also be utilized. The cosolvents are particularly useful for solubilizing the oils utilized in the compositions of the invention and, especially, for reducing the need for high concentrations of surfactants which may cause skin irritation. Normally, a cosolvent will be employed if the composition contains more than 1% oils. Cosolvents are typically employed at concentrations of from about 0% to about 40%, preferably 10% to 25%.

CLARIFIERS AND DETACKIFIERS

The compositions may contain small amounts of one, or several, emollients, surfactants and other water insoluble components which may additionally function as auxilliary solvents to increase clarity or as antitacking agents to prevent stickiness of the compositions after they have dried on the skin surface. Emollients enhance the feel of the compositions and the ease with which they can be applied. Emollients include oils, lubricants and other materials used to enhance the product's organoleptics, as is well known in the art.

The compositions may additionally contain semipolar products which are soluble or compatible with propylene glycol and which are known to those skilled in the art and can be utilized in the practice of this invention. Clear, liquid, semipolar emollients and surfactants are presently preferred to attain improved clarity under all temperature conditions.

One class of compounds meeting the above description is disclosed in U.S. Pat. No. 4,759,924. Certain of them are commercially available under the trade names PPG-5-Ceteth 20 (available as Procetyl AWS), PPG-3-Myreth-3, PEG-20-Laurate and Poloxamer 335.

The following Table lists other semipolar materials which may be employed. They are identified by their trade names the CTFA Dictionary Name and the commercial source of the material.

TABLE 2

| Trade Name | CTFA Name | Source |
|---|---|---|
| 1. Arosurf 66-E2 | Isosteareth-2 | Sherex |
| 2. Arlasolve 200 | Isoceteth-20 | ICI |
| 3. Dermol G-76 | Glycereth-7-Benzoate | Alzo |
| 4. Brij 30 | Laureth-4 | ICI |
| 5. Arosurf 66PE12 | PPG-3-Isosteareth-9 | Sherex |
| 6. Cetiol HE | PEG-7-Glyceryl Cocoate | Henkel |
| 7. Aethoxal B | PPG-5-Laureth-5 | Henkel |
| 8. Emulgin L | PPG-2-Ceteareth-9 | Henkel |
| 9. Sandoxylate SX-408 | PPG-2-Isoceteth-4 | Sandoz |
| 10. Sandoxylate SX-424 | PPG-2-Isoceteth-12 | Sandoz |

Other useful materials having the desired properties which can be employed in the invention include diisopropyl sebacate, myristyl lactate and isopropyl myristate.

Clarifiers and tackifiers as employed in the practice of this invention are typically at a concentration level of from about 1.5% to about 12%, preferably 1.5% to 8%.

When desired, stick hardness can be improved by the addition of cetyl alcohol. If employed, it will not be at amounts in excess of 1% in order not to adversely affect transparency. The cetyl alcohol if employed, is used in an amount up to about 1.0%, preferably 0.3 to 0.7%.

A small quantity of non-polar emollients may optionally be included in the instant compositions. Suitable non-polar emollients include fatty acid esters and diesters, volatile silicones (cyclomethicone), dimethicone, vitamin E, natural oils and hydrocarbons such as isodecane. If a non-polar emmollient is employed, it is used in an amount up to about 10%. At concentrations above this level, clarity of the stick may be adversely affected. Typically useful emollients of this class are disclosed in U.S. Pat. No. 4,781,917.

BENZALDEHYDE SCAVENGER

As stated above, DBMSA tends to decompose in acid solution to produce benzaldehyde which imparts an undesirable odor or color. Such decomposition may be inhibited by increasing the basicity of the compositions utilizing increased amounts of alkaline stabilizers. This is the preferred procedure. However, it may be useful to add small amounts of a compound which will react with the benzaldehyde to produce a colorless product which should also, of course, be substantially odorless. Such products are polyhydroxy aliphatic polyhydric alcohols containing 3 to 6 carbon atoms. They form acetals with the benzaldehyde. The preferred reactant is glycerin. Another useful product is sorbitol. If employed, the benzaldehyde scavenger will be at a concentration of up to about 10%. The preferred range is 0.2% to 5%. The term "polyhydroxy" is used herein to define aliphatic alcohols containing from 3 to 6 carbon atoms and containing at least three hydroxyl groups. The term is used to distinguish the scavenger from the solvents and cosolvents.

THE PERFUMES

The perfumes normally employed in cosmetic compositions such as those of this invention may be employed herein if desired. Typical perfumes are illustrated in the examples. The concentration of perfume will typically be up to about 2%, preferably from about 0.5% to 2%.

THE ANTIBACTERIAL AGENTS

The antibacterial agents which may be utilized in the practice of this invention, if desired, will be the same as are normally employed in compositions of this nature. They include, for example, triclosan, benzethonium chloride and zinc phenolsulfonate. Typically, the compositions may contain up to about 2% antibacterial agent, preferably about 0.1% to 1.5%.

The compositions may additionally contain coloring agents, botanicals and other components normally employed in such compositions provided they are compatible with the other components in the compositions.

An important factor in the stability and clarity of the products of this invention is the miscibility of the various components. It is important, therefore, that the antiperspirant be dissolved in the final composition.

There are several procedures for assuring that the antiperspirant is in solution. These will be illustrated by reference to the preferred antiperspirant for use in the invention, namely aluminum zirconium tetrachlorohydrate glycine-propylene glycol which is commercially available as Rezal 36 GPG.

Rezal 36 GPG is a powder which can be dissolved by heating in propylene glycol to produce a 20% to 25% solution. The solution may be employed in an appropriate amount to produce the final composition.

Regular aluminum zirconium tetrachlorohydrate glycine powder (Rezal 36 GP), and other such products, are not normally soluble in propylene glycol (e.g. Dow Corning AZG369 and Westchlcr ZR35B). However, aqueous solutions containing from about 35% to 60% of an aluminum zirconium polychlorohydrate or a glycine complex can be dissolved in propylene glycol for incorporation in the final formulation.

In the process, an aqueous solution of the antiperspirant (e.g. a solution at a concentration of about 50% to 60%) is mixed with a selected amount of propylene glycol and the water evaporated, suitably by heating to produce a clear propylene glycol solution substantially free of water. Sufficient propylene glycol should be employed so that evaporation of substantially all of the water leaves a propylene glycol solution containing the amount of antiperspirant salt required in the final antiperspirant composition.

The same propylene glycol solution may be prepared with the commercially available 50% aqueous antiperspirant solution.

Aluminum chlorohydroxide is available as a 50% aqueous solution which can be similarly converted to a propylene glycol solution of the desired concentration. The same is true of aluminum zirconium tetrachlorohydrate-glycine 50% aqueous solutions, such as Rezal 36G concentrate, Westchlor ZR41 and Dow Corning AZGX 51226.

Typical processes by which the compositions of the invention are produced are illustrated in the examples. Generally, heat is required to solubilize the various ingredients. It has been observed that the optimum time/temperature relationship for heating the antiperspirant and the gelling agent is from about 215° F. to 240° F. for from about 5 to about 60 minutes. However, with specific antiperspirants the optimum time/temperature relationship may vary. Generally, with the Al/Zr polychlorohydrates, it is best to use shorter times and lower temperatures.

The compositions of this invention, when tested substantially as described in Federal Register, Vol. 43, Number 196, Oct. 10, 1978, are as active as commercially available compositions containing substantially larger amounts of antiperspirant.

The following examples are given by way of illustration only and are not to be considered limitations of this invention, many apparent variations of which may be made without departing from the spirit or scope thereof.

The examples illustrate an aspect of this invention which is very important for the production of transparent gel sticks. In the process of the invention, preferably, formula amounts of the antiperspirant and the stabilizing alkaline reagent are heated together in the formula amount of the propylene glycol to produce a first mixture as a clear solution. The DBMSA is then added to the first mixture. The other components are mixed and heated separately to produce a second mixture. The two mixtures are then combined to produce the final product which is cooled and gelled in an appropriate mold, e.g. a mold suitable for the formation of a standard antiperspirant stick. It should be noted that glycerin can be added after the DBMSA or into the first or second mixture as desired. The key feature of the process is that the DBMSA be introduced into a composition already containing the stabilizer. If this is not done it is highly likely that the composition will not gel.

EXAMPLE 1

The following components were mixed, as described below, to prepare a composition of this invention.

| Ingredient | % (W/W) |
| --- | --- |
| Propylene Glycol | 58.95 |
| Al/Zr Tetrachlorohydrate Gly.- Propylene Glycol Powder (Rezal 36GPG - Reheis) | 12.00 |
| Sodium Hydroxide - Pellets ACS grade | 0.90 |
| Dibenzylidene Monosorbitol Acetal - 925 | 2.50 |
| Glycerin USP | 0.75 |
| Dipropylene Glycol | 18.00 |
| Glycereth-7-Benzoate | 1.50 |
| PPG-3-Isosteareth-9 | 1.50 |
| PPG-3-Myristyl Ether | 3.00 |
| FD&C Blue #1(0.1% Propylene Glycol Sol'n.) | 0.40 |
| Perfume | 0.50 |
|  | 100.00 |

1. Add 29.95 parts of Propylene Glycol to a suitable vessel equipped with a Premier Mixer and a Cowles Dissolver. Heat to 200° F.
2. Add Al/Zr Tetrachlorohydrate Gly-Propylene Glycol Powder and mix until clear.
3. Add 29 parts of Propylene Glycol and Sodium Hydroxide to a separate vessel and heat to 240° F. Mix until clear.
4. Add Step 3 to Step 2 and heat to 240° F. while mixing.
5. Add Dibenzylidene Monosorbitol Acetal - 925 (sieved) slowly to the batch and mix until clear. Add glycerin and mix for 15 minutes.
6. Cool the batch to 200° F.
7. Add Dipropylene Glycol, Glycereth-7-Benzoate, PPG-3-Isosteareth-9, PPG-3-Myristyl Ether and FD&C Blue #1 solution to a separate vessel and heat to 200° F.
8. Add Step 7 at 200° F. to Step 6 at 200° F. Cool to 175° F. to 180° F. while mixing.
9. Add perfume to batch at 175° F. to 180° F. and mix gently.
10. Pour the product into containers when the batch is 155° F. to 165° F.

EXAMPLE 2

A composition of the invention was prepared by mixing the following ingredients as described.

| Ingredients | % (W/W) |
| --- | --- |
| Propylene Glycol | 63.57 |
| ACH - Propylene Glycol Complex (Rehydrol II-Reheis) | 12.00 |
| Sodium Hydroxide Pellets, ACS grade | 0.63 |
| Dibenzylidene Monosorbitol Acetal-925 | 2.25 |
| Dipropylene Glycol | 18.00 |
| Glycerin, USP | 0.50 |
| Glycereth-7-Benzoate | 0.75 |
| Dimethicone Copolyol - 193 | 1.50 |
| Color FD&C Blue #1 (0.1% Propylene Glycol Solution) | 0.30 |
| Perfume | 0.50 |
|  | 100.00 |

1. Add 34.57% of the formula weight of Propylene Glycol into a suitable mixing vessel and begin to heat to 237°±3° F. Add ACH - Propylene Glycol Complex and mix with a Premier mixer attached with a Cowles dissolver. Continue mixing for the entire manufacturing process.

2. Add 29% of the formula weight of Propylene Glycol into a suitable mixing vessel and begin to heat to 237°±3° F. Add sodium hydroxide and mix until a clear solution is obtained. (Do not exceed 240° F.). Add to batch at 237°±3° F. and mix batch rapidly for 15 minutes at 237°±3° F.

3. Add Dibenzylidene Monosorbitol Acetal 925 slowly to Batch at 237° F.±3° F. Maintain at 237° F.±3° F. for 45 minutes while mixing rapidly. Cool batch to 210° F. while mixing gently.

4. Add Dipropylene Glycol, Glycerin, Glycereth-7-Benzoate, Dimethicone Copolyol-193, and FD&C Blue #1 (0.1% Propylene Glycol Solution) to a separate vessel and heat to 210° F.

5. Add Step 4 ingredients to batch and cool to 180° F. while mixing gently.

6. Add perfume at batch temperature of 180° F. while mixing gently.

7. Pour into containers.

EXAMPLE 3

A third composition of the invention was prepared from the components listed using the procedure described below.

| Ingredient | % (W/W) |
| --- | --- |
| Propylene Glycol | 55.7 |
| Al/Zr Tetrachlorohydrate Gly- Propylene Glycol Powder (Rezal 36GPG - Reheis) | 12.0 |
| Glycerin USP | 1.0 |
| Sodium Bicarbonate Powder, USP | 1.5 |
| Dibenzylidene Monosorbitol Acetal-925 | 2.5 |
| Dipropylene Glycol | 15.0 |
| Isosteareth-2 | 2.0 |
| Ceteth-2 | 1.0 |
| Cetyl Alcohol N.F. | 0.5 |
| PPG-3-Myristyl Ether | 4.0 |
| Diisopropyl Sebacate | 2.0 |
| Myristyl Lactate | 2.0 |
| FD&C Blue #1 (0.1% Propylene Glycol Soln.) | 0.3 |
| Perfume | 0.5 |
| | 100.0 |

1. Heat the Propylene Glycol to 180° F.

2. Slowly add the Al/Zr Tetrachlorohydrate Gly - Propylene Glycol to Part 1 while mixing well with a Premier mixer attached with a Cowles Dissolver until the batch is clear. Heat the clear mixture to 220° F.

3. When Part 2 has reached 220° F., add the Glycerin.

4. Divide the sodium bicarbonate into three portions. Very slowly add the first portion to Part 3, which is under agitation. This will take approximately 10 minutes. When the batch is clear, add the next portion of sodium bicarbonate in the same manner. Heat the batch to 240° F. until all of the sodium bicarbonate has been added and the batch is clear.

5. Slowly add the Dibenzylidene Monosorbitol Acetal 925 to Part 4 and mix at 238°±2° F. until the batch is clear, heat the batch to 240° F. (about 15 minutes).

6. Cool the batch to 200° F.

7. In a separate container, mix and gently heat to 200° F., the Dipropylene Glycol, Isosteareth-2, Ceteth-2, Cetyl Alcohol, PPG-3-Myristyl Ether, Diisopropyl Sebacate, Myrissyl Lactate, and FD&C Blue #1 (0.1% Solution in Propylene Glycol).

8. Add Part 7 to Part 6 (both at 200° F.) and mix well until the batch is homogeneous. Then cool the batch to 165°±5° F.

9. Add the perfume to Part 8 and mix well. At this point the gelling temperature should be checked in a 30 ml. size beaker.

10. Pour the batch into containers at a temperature about 20° F. above the gelling temperature determined in Part 9.

EXAMPLE 4

The following components were mixed to prepare a composition of this invention useful for the preparation of deodorant sticks.

| Ingredient | % (W/W) |
| --- | --- |
| Propylene Glycol | 54.45 |
| ACH-Propylene Glycol Complex | 6.00 |
| Glycerin | 1.00 |
| Sodium Bicarbonate | 0.80 |
| Dibenzylidene Monosorbitol Acetal-925 | 2.20 |
| Dipropylene Glycol | 25.00 |
| Isosteareth-2 | 2.00 |
| Ceteth-2 | 1.00 |
| Diisopropyl Sebacate | 1.00 |
| Myristyl Lactate | 1.00 |
| PPG-3-Myristyl Ether | 4.00 |
| Triclosan | 0.25 |
| FD&C Blue #1(0.1% P.G.) | 0.30 |
| Perfume | 1.00 |
| | 100.00 |

EXAMPLE 5

A composition of the invention useful for the production of deodorant sticks was prepared by mixing the following ingredients:

| Ingredient | % (W/W) |
| --- | --- |
| ACH-Propylene Glycol Complex | 6.00 |
| Propylene Glycol | 57.35 |
| NaOH | 0.35 |
| Glycerin | 0.75 |
| Dibenzylidene Monosorbitol Acetal-925 | 3.00 |
| Dipropylene Glycol | 25.00 |
| PPG-3-Isosteareth-9 | 1.50 |
| PPG-3-Myristyl Ether | 3.00 |
| Glycereth-7-benzoate | 1.50 |
| FD&C Blue #1(0.1% P.G.) | 0.30 |
| Triclosan | 0.25 |
| Perfume | 1.55 |
| | 100.00 |

What is claimed is

1. A stable, substantially anhydrous, transparent, gelled antiperspirant stick composition for application to human skin, said composition being substantially free of lower aliphatic monohydroxy alcohols and comprising by weight, based on the total weight of the composition:

a: an effective antiperspirant amount of an acidic metallic antiperspirant salt soluble in the composition;

b: from about 41% to about 75% of a dihydroxy aliphatic alcohol solvent containing from 3 to 5 carbon atoms;

c: from about 0% to about 40% of a dihydroxy aliphatic ether containing from 6 to 10 carbon atoms;

d: an effective amount of dibenzylidene monosorbitol acetal sufficient to gel the composition;

e: from about 1.5% to about 12% of a clarifier and/or detackifier;

f: from about 0% to about 10% of a polyhydroxy aliphatic alcohol containing from 3 to 6 carbon atoms;

g: from about 0% to about 1.0% of cetyl alcohol, h: from about 0.1% to about 2% of an alkaline stabilizer which is an alkali or alkaline earth metal oxide, hydroxide, carbonate or bicarbonate or a trivalent metallic hydroxide, or mixtures thereof;

i: from about 0% to about 2% of an antibacterial agent; and j: from about 0% to about 2% of a perfume.

2. A composition as in claim 1 wherein the antiperspirant is aluminum zirconium polychlorohydrate glycinepropylene glycol.

3. A composition as in claim 1 wherein the stabilizer is sodium hydroxide, sodium bicarbonate or potassium hydroxide and the antiperspirant is aluminum zirconium polychlorohydrate glycinepropylene glycol.

4. A composition as in claim 1 additionally containing from about 0.20% to about 5.0% of glycerin.

5. A stable, substantially anhydrous, transparent, gelled antiperspirant stick composition for application for human skin, said composition being substantially free of lower aliphatic monohydroxy alcohols and comprising by weight, based on the total weight of the composition:

a: an effective antiperspirant amount of an acidic metallic antiperspirant salt soluble in the composition;

b: from about 51% to about 70% of a dihydroxy aliphatic alcohol solvent containing from 3 to 5 carbon atoms;

c: from about 0% to about 40% of a dihydroxy aliphatic ether containing from 6 to 10 carbon atoms;

d: an effective amount of dibenzylidene monosorbitol acetal sufficient to gel the composition;

e: from about 1.5% to about 8% of a clarifier and/or detackifier;

f: from about 0.2% to about 5% of a polyhydroxy aliphatic alcohol containing from 3 to 6 carbon atoms;

g: from about 0% to about 1.0% of cetyl alcohol, h: from about 0.4% to about 1.5% of an alkaline stabilizer which is an alkali or alkaline earth metal oxide, hydroxide, carbonate or bicarbonate or a trivalent metallic hydroxide, or mixtures thereof;

6. A composition as in claim 5 wherein the antiperspirant is aluminum zirconium polychlorohydrate glycinepropylene glycol.

7. A composition as in claim 5 wherein the stabilizer is sodiumhydroxide, sodium bicarbonate or potassium hydroxide and the antiperspirant is aluminum zirconium polychlorohydrate glycinepropylene glycol.

8. A composition as in claim 5 additionally containing from about 0.2% to about 5.0% glycerin.

* * * * *